US00PP07803P

United States Patent [19]

Pellett

[11] Patent Number: Plant 7,803

[45] Date of Patent: Feb. 25, 1992

[54] RED MAPLE TREE NAMED AUTUMN SPIRE

[75] Inventor: Harold M. Pellett, Mound, Minn.

[73] Assignee: Regents of the University of Minn., Minneapolis, Minn.

[21] Appl. No.: 527,031

[22] Filed: May 22, 1990

[51] Int. Cl.[5] ..... A01H 5/00

[52] U.S. Cl. ..... Plt./51

[58] Field of Search ..... Plt. 51

[56] References Cited

U.S. PATENT DOCUMENTS

P.P. 5,053 5/1983 Pellet et al. ..... Plt. 51

*Primary Examiner*—James R. Feyrer

[57] ABSTRACT

A red maple tree which exhibits an upright broad-columnar form, early autumn maturity, good winter hardiness, excellent red autumn leaf color, and seedlessness.

3 Drawing Sheets

ORIGIN OF THE CULTIVAR

The present invention relates to a new and distinct variety of red maple tree, *Acer rubrum*. The variety was selected from a seedling population grown from open-pollinated seed at an arboretum located in Carver County, Chanhassen, Minn.

*Acer rubrum* is a deciduous tree native to the eastern United States, growing in the wild from Florida to southern Canada. It is commonly referred to as red maple and is highly valued as a shade tree, due to the ornamental character of its autumn foliage, bark and flowers.

The autumn leaf color of native stands of red maple varies considerably from yellow to bright red. There is also substantial variation in tree form. Numerous selections have been made and introduced to the nursery trade, particularly varieites having superior form and fall leaf color. However, most cultivars available in the nursery trade are generally unsuitable for northern states because they lack sufficient cold hardiness and/or fail to develop desirable autumn leaf color prior to the occurrence of damaging frosts.

The plot of seedlings from which this variety was selected were sown some 22 years ago in a cultivated area located at the above-noted arboretum in Carver County, Minn. The female parent of the seedling population grew in the wild near the Experiment Station, located at Grand Rapids, Minn., and was observed to consistently develop good autumn leaf color. Selection of the present variety was based upon observations that it possessed a broad-columnar crown form, excellent red autumn leaf color, winter hardiness in Minnesota, and other desirable characteristics such as early fall maturity and leaf coloring and absence of seeds or fruit.

Following continued observations and testing of the variety for several years, I am convinced that this cultivar is a novel and improved variety indicated by the following unique combination of qualities and characteristics which distinguish this variety from all other known varieties of red maple trees known to the inventor.

SUMMARY OF CHARACTERISTICS

The present variety has been named Autumn Spire and will subsequently be introduced to the nursery trade. The unique combination of characteristics of this cultivar are as follows:

(1) Upright form. The present variety produces a tree with ascending branches and a broad-columnar crown form particularly suited to landscape situations where limited crown spread is desirable. The variety develops a strong central leader.

(2) Early fall maturity and winter hardiness. The present variety matures in early autumn with its leaves coloring at a date earlier than most other known specimens and varieties of *Acer rubrum* grown in Minnesota and other northern states of similar climate. This early autumnal maturity contributes to the winter hardiness of the present variety in Minnesota and other northern states of similar cold climate.

(3) Good fall leaf color. This cultivar exhibits a bright red autumn coloring of its leaves which is better or more red than average in comparison to other known varieties of *Acer rubrum*.

(4) Seedlessness. The present variety has only staminate flowers and therefore produces no seed nor fruit.

ASEXUAL REPRODUCTION

The present variety has been asexually reproduced by means of rooted softwood cuttings and also by the grafting of budding stuck by a nursery located at 1325 Bailey Road, St. Paul, Minn. Such asexual reproduction confirms that the characteristics and qualities of this variety described herein are true to form and consistent throughout succeeding vegetating propagation.

SUMMARY OF THE CULTIVAR

The accompanying drawings comprise photographs showing characteristics of this new variety. The photographs were taken of a specimen of the variety growing at the above-noted arboretum in Carver County, Minn. The accompanying photographs depict features or characteristics of the present variety as true as reasonably possible.

Figure 1:
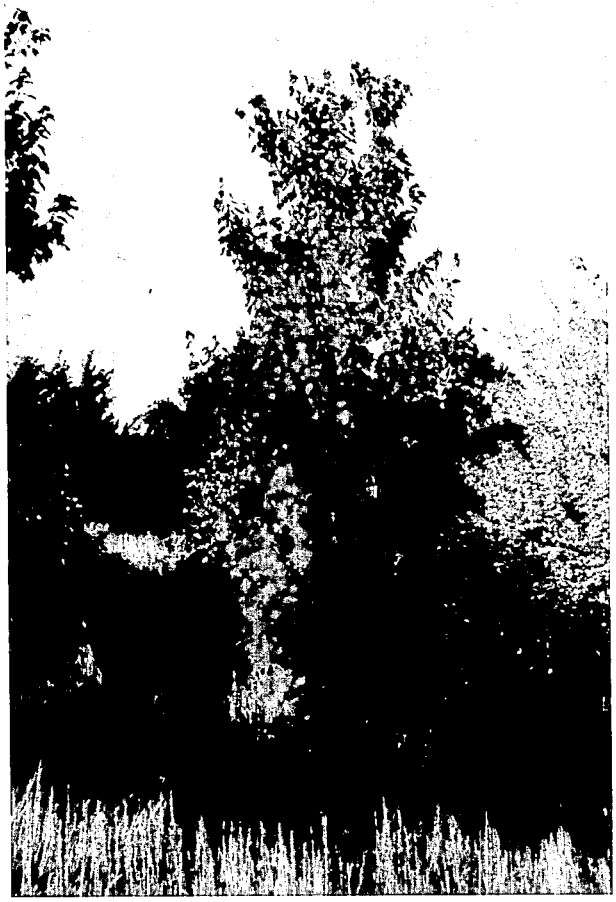
FIG. 1 is a photo of the full form of the tree described herein.
Figure 2:
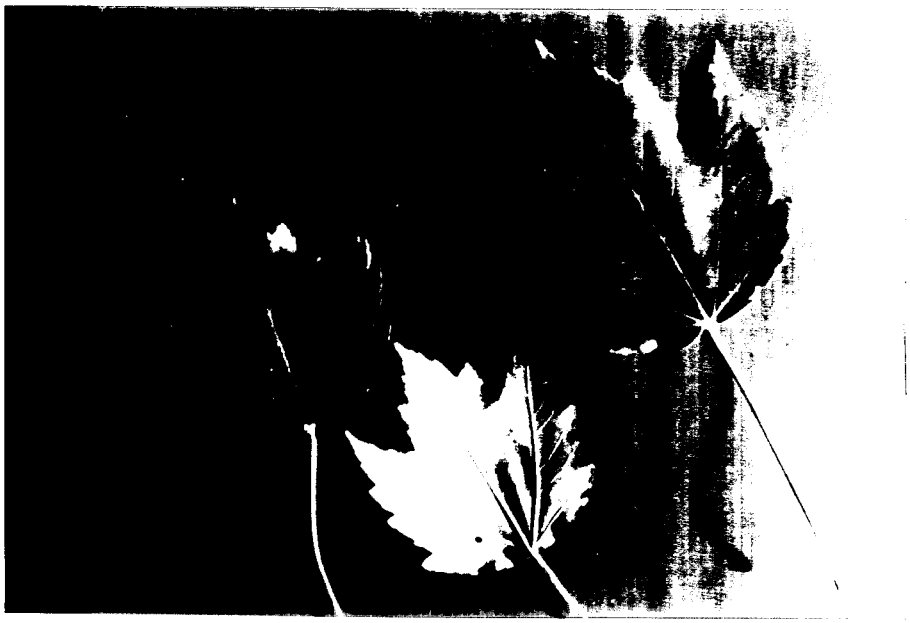
FIG. 2 is a photo showing both sides of typical leaves with initial autumn coloration.
Figure 3:
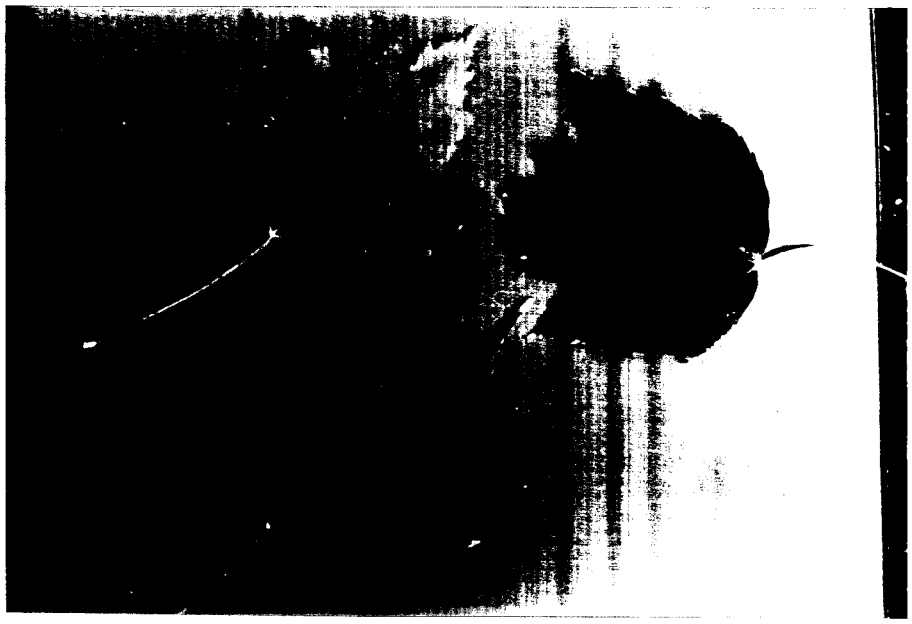
FIG. 3 is a photo of three leaves showing subsequent autumn coloration.
Figure 4:
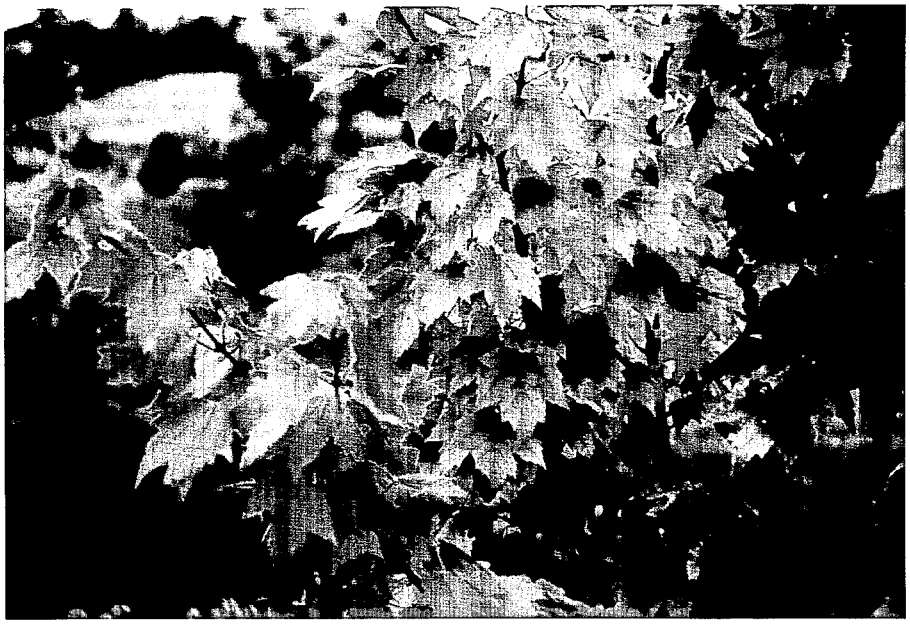
FIG. 4 is a photo of tree branches at near peak autumn coloration, indicating more coloration in outer branches.
Figure 5:
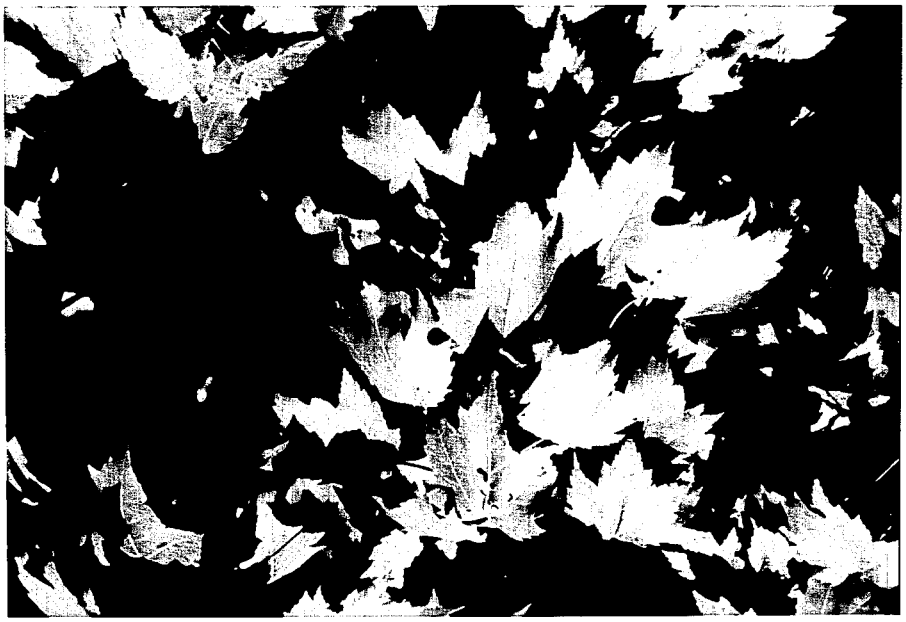
FIG. 5 is a photo of leaves and branches showing mid-summer leaf coloration and form.

Following is a detailed description or specification of the present variety. References to color relate to *The Royal Horticultural Society Colour Chart,* 1966 Edition, noted herein as R.H.S., except for color terms of ordinary dictionary meaning which may occasionally be referred to.

Parentage: The present variety was produced from a seedling of open-pollinated seed obtained from an unnamed variety of *Acer rubrum* growing in the wild near the Experiment Station located at Grand Rapids, Minn.

Propagation: The present variety has been asexually reproduced by rooting of softwood cuttings and grafting of budding stock and has retained the distinguishing characteristics described herein through succeeding propagations. The location where the present variety has been primarily grown and observed is the above-noted arboretum located in Carver County, Minn. and the above-noted nursery located on Bailey Road in St. Paul, Minn., whereat the variety has been observed in controlled plots.

Tree

Form and growth habit: The present variety exhibits a broad-columnar habit with a narrower crown than is typical of the species. The variety develops a strong dominant central leader. Consequently, the variety is more useful than other known hardy varieties of *Acer rubrum* for landscape situations where limited crown spread is desirable.

Trunk: Moderately stout. Moderately rough.

Branches: Ascending, forming approximately 25 degree angles with the trunk. Side branches arise from the leader at a typical crotch angle of approximately 30° to 35°. As the branches elongate they turn upward somewhat to develop a narrow crown. The side branches in the upper portion of the tree grow at an angle less than 30° away from the central leader. Winter color of one-year stem corresponds to R.H.S. 178A.

Height: The original tree is now approximately 30 feet high and 8 feet wide at 22 years of age. It is growing in heavy sod in a research plot at the above-noted arboretum in Carver County, Minn.

Lenticels: Average size and density.

Foliage: Three-lobed leaves with truncate to cordate bases. Serrate margins with approximately 2.5 serrations/cm.

*Leaf blades.*—Leaf blades average 9.0 cm (range of 8.4 to 11.0 cm) in width and 9.9 cm (range of 8.5 to 13.2 cm) in length.

*Petioles.*—Petioles average 6.7 cm in length (range of 5.9 to 8.3 cm).

*Summer leaf color.*—Upper side of leaf blade is R.H.S. 146B and glabrous. Lower side of leaf blade is R.H.S. 192A and glaucous with scattered hairs. There appears to be slight variation in the color of the upper side of the leaf blade, depending upon season and natural variation.

*Fall leaf color.*—The variety is subject to some variation in fall leaf color depending on seasonal climatic conditions. Under average conditions, leaf color develops progressively from a deep purple-red (R.H.S. 184A on Sept. 28, 1989 at the above-noted arboretum in Carver County, Minn). to a bright red (R.H.S. 46A on Oct. 2, 1989) at its peak.

Flower buds:

*Size.*—3 mm long.

*Shape.*—Roundish obovate.

*Color.*—Bud scales are R.H.S. 187A.

Flowers:

*Date of bloom.*—Typically mid to late April in the Minnesota locality noted above.

*Quantity.*—Average for the species.

*Overall size.*—Average 1.4 cm from base of pedicel to tip of anthers.

*Sex.*—Staminate. The present variety has no female flower parts and produces no seeds or fruits.

*Color.*—Overall effect of corolla is R.H.S. 46C. The flowers, which open prior to the foliage, provide some early color, and the flower color of the variety is darker than typical for the species. As the flowers open, the bud scales expand and open. Several (typically five or six) individual flowers on 1.2 cm. long pedicels arise from the base. Petals of the individual flowers are quite small with open diameter of the corolla approximately 3 mm. Anthers extend upward from the corolla approximately 5–6 mm. Overall size of each flower cluster is approximately ¾ cm. wide and 1.5 to 2 cm. high.

Dormant flower and leaf buds: Dormant flower and leaf buds and leaf scars are typical of the species. Winter color of imbricate scales of leaf buds correspond to R.H.S. 184A. Average length of the dormant buds is 3–4 mm. The crescent shaped leaf scars are light gray in color and extend to almost meet with the opposite scar.

Seeds: None, as determined from observation of mature tree which is 22 years old. The present variety is seedless because it has no female flower parts to produce fruit.

Winter hardiness and early autumn maturity: This variety matures earlier in the autumn and exhibits leaf coloring at a date earlier than other known varieties of *Acer rubrum* grown in the same area. Such early maturity is believed to result in greater winter hardiness and absence of winter injury in the form of tip die-back of branches, which is common for many other varieties of *Acer rubrum* grown in the Minnesota area noted herein.

The variety of Red Maple most similar to this variety Autumn Spire in hardiness is Northwood Red Maple (U.S. Plant Pat. No. 5,053) which matures only a few days later in the fall and also has excellent hardiness in northern states. The two varieties differ markedly in plant form. Northwood has a much broader crown with wider branch angle. Thus the two varieties fit different landscape situations. Autumn Spire also has a superior fall leaf coloration with a more intense red color at its peak.

I claim:

1. A new and distinct variety of red maple tree, substantially as shown and described herein, characterized particularly as to novelty by the unique combination of an upright broad-columnar form, early autumn maturity, good winter hardiness, excellent red autumn leaf color, and absence of seeds.

* * * * *